United States Patent [19]

Pesque et al.

[11] Patent Number: 4,714,846

[45] Date of Patent: Dec. 22, 1987

[54] APPARATUS FOR THE EXAMINATION OF OBJECTS WITH ULTRA-SOUND, COMPRISING AN ARRAY OF PIEZO-ELECTRIC TRANSDUCER ELEMENTS

[75] Inventors: Patrick R. Pesque, Perigny; Jean-Marie C. Nicolas, Paris, both of France

[73] Assignee: U.S. Philips Corporation, New York, N.Y.

[21] Appl. No.: 921,982

[22] Filed: Oct. 22, 1986

[30] Foreign Application Priority Data

Oct. 25, 1985 [FR] France ................. 85 15849

[51] Int. Cl.$^4$ ........................................... H01L 41/08
[52] U.S. Cl. .................................... 310/317; 310/319; 310/334; 310/368
[58] Field of Search .......................... 310/334–337, 310/317, 361, 368, 319; 128/660–663; 73/632, 642

[56] References Cited

U.S. PATENT DOCUMENTS

| | | | |
|---|---|---|---|
| 4,101,795 | 7/1978 | Fukumoto et al. | 310/336 |
| 4,139,793 | 2/1979 | Michel | 310/368 X |
| 4,211,948 | 7/1980 | Smith | 310/334 X |
| 4,242,912 | 1/1981 | Burckhardt et al. | 310/334 X |
| 4,247,797 | 1/1981 | Echigo et al. | 310/361 |
| 4,305,014 | 12/1981 | Borburgh et al. | 310/334 |
| 4,525,647 | 6/1985 | Dworsky | 310/361 |
| 4,550,606 | 11/1985 | Drost | 310/334 X |
| 4,603,276 | 7/1986 | Coursant | 310/334 X |

OTHER PUBLICATIONS

Hybrid Linear and Matrix Acoustic Arrays, by M. Pappalardo, *Ultrasonics*, Mar. 1981, pp. 81-86.
An Acoustic Transducer Array for Medical Imaging–Part 1, by John D. Larson, III, Hewlett–Packard Journal, vol. 34 (1983) Oct., No. 10, Amstelveen, Nederland, pp. 17-22.

*Primary Examiner*—Mark O. Budd
*Attorney, Agent, or Firm*—Jack E. Haken

[57] ABSTRACT

An apparatus for the examination of objects with ultrasound, comprising a linear or two-dimensional array (10) of piezo-electric transducer elements (10 (1), . . . , 10 (n)) with a length L and a width W, a stage for the repeated transmission of ultrasonic signals and a stage for the reception and processing of the ultrasonic echoes received. The thickness T of the elements is equal to half the wavelength corresponding to a first frequency F for which there exists, on the two-dimensional diagram of the curves $F \cdot T = f(W/T)$, or respectively, on the three-dimensional diagram of the curves $F \cdot T = f(W/T, L/T)$ of the distribution of the resonance frequencies, a first vibratory mode at the said first frequency F and a second vibratory mode at a second frequency equal to or near 2F. The transmission stage incorporates a generator (20) of excitation signals at the first frequency F, the spectrum of these excitation signals excluding at least the second frequency.

2 Claims, 4 Drawing Figures

APPARATUS FOR THE EXAMINATION OF OBJECTS WITH ULTRA-SOUND, COMPRISING AN ARRAY OF PIEZO-ELECTRIC TRANSDUCER ELEMENTS

The present invention relates to an apparatus for the examination of objects with ultrasound, comprising a linear array of piezo-electric transducer elements with a width W, associated with a stage for the repeated transmission of ultrasonic signals for the excitation of the transducers and with a stage for the reception and processing of the ultrasonic echoes corresponding to obstacles encountered in their direction of propagation by the transmitted signals. This apparatus is mainly for use in the medical field for the echographic examination of biological tissue but also in the field of non-destructive testing of materials.

At present, in the field of ultrasonography and particularly during ultrasonic examinations of biological tissue as an aid to diagnosis, efforts are increasingly directed at gathering quantitative information on the organs or tissues examined, this aim being achieved by the local evaluation of one or more parameters such as the differential coefficient $\beta$ of ultrasonic attenuation or the coefficient B/A of acoustic non-linearity, and at observing the variations of these parameters in the objects examined. These evaluations and variations in fact yield definite indications as to the nature of these objects and their pathological condition.

The non-linearity of objects and particularly that of biological tissues is demonstrated as follows. During its passage through the object, the train of ultrasonic waves transmitted at a particular frequency generates at each point and in the same direction an ultrasonic wave of a frequency which is double that of transmission and whose amplitude is linked to the value of the coefficient B/A (A and B are respectively the linear and quadratic coefficients in the expression formulating the relation between the pressure variations and the density variations in the object under examination).

The echographic examining apparatus must therefore, in this case, be equipped with a wideband transducer configuration covering at least one octave. In the case of narrow-band excitation, the conventional wideband structures, of the type with several interferential adaptation layers (or quarter-wave layers), are unfortunately not very sensitive, which is unfavorable to employment of the application envisaged here, in which the received signal is of a relatively weak amplitude.

It is therefore an object of the invention to propose an apparatus for the examination of objects with ultrasound, whose transducer configuration gives good sensitivity at at least two frequencies situated substantially an octave from each other, in order to permit a correct quantitative evaluation of the coefficient B/A of non-linearity of the objects.

To that end the apparatus according to the invention is characterized in that the thickness T of the said transducer elements is equal to half the wavelength corresponding to a first frequency F for which there exists, on the two-dimensional diagram of curves $F \cdot T = f(W/T)$ of the distribution of the resonant freqencies, a first vibratory mode at the said first frequency F and a second vibratory mode at a second frequency equal or adjacent to 2F, the transmission stage comprises a generator of excitation signals at the first frequency and the spectrum of these excitation signals excludes the second frequency.

U.S. Pat. No. 4,101,795 describes a transducer configuration whose piezo-electric elements can vibrate in purely a thickness mode, without undesirable coupling with interfering vibratory modes. In the case of the transducer configuration according to the current invention it is also desired to have a single vibratory mode during the transmission, but a particular geometry of the structure is chosen such that during reception, instead of eliminating, as is generally desired, all vibratory modes other than that wanted during transmission, one of them is retained preferentially, namely a mode with resonance at a frequency double the transmission frequency.

For ultrasonic transducers used for medical imaging it is usually required that the response of the transducers should be short, in order to obtain good resolution. Within the framework of the present invention, this shortness has been sacrificed but, in return, during the reception there is obtained a resonance of the piezo-electric material (i.e. good sensitivity of the transducer configuration) at twice the frequency of transmission, a frequency at which the non-linear effect which it is desired to observe is produced. Having this good sensitivity at the said frequency is in fact an advantage in several respects since the signal to be detected at this double frequency is on the one hand of low amplitude and on the other particularly attenuated by the object under examination in comparison with the transmission signal at half its frequency (the degree of attenuation increases with frequency).

The invention wil now be explained in detail with reference to the drawings, in which:

FIG. 1 shows an example of a Fabian-Sato diagram showing a family of curves representing the districution of the resonance frequencies of piezo-electric material when this material is of piezo-electric ceramic of the PZT type (for example, PXE-5), each mode shown in this diagram being in fact characterized by two curves, one corresponding to the piezo-electric resonance frequencies (lower curve) and the other to the anti-resonance, or stiffened elastic resonance, frequencies (top curve);

A knowledge of the modes of vibration of piezo-electric transducer elements may be put into effect theoretically by modelling or experimentally by characterizing the piezo-electric material, in the latter case by establishing the relations between the various parameters on which the transducer structure formed with this material depends. These relations can be visualized particularly in the form of so-called Fabian-Sato diagrams (see FIG. 1) which show the curves representing the distribution of the resonant frequencies of the material concerned. For the various modes of vibration, fundamental and harmonic, of the material, these curves show the relation between the ratio W/T and the product F·T of the thickness-mode resonant or anti-resonant frequency, as the case may be, of the transducer elements. They make it possible to determine the geometrical characteristics of these elements as a function of that one of the modes which it is in fact desired to obtain.

Examination of such a family of curves provides in particular a guide to the choice of the ratio W/T to use in order to obtain single-mode operation of the transducer structure, which is the mode of operation traditionally aimed at.

Figure 2:
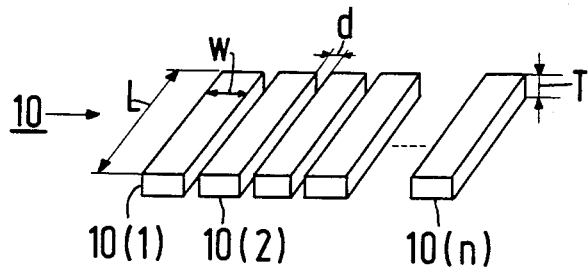
FIG. 2 shows a linear network of transducer elements.

As shown in FIG. 2, in the proposed embodiment the apparatus for examining objects by echography comprises first of all an array 10 of ultrasonic transducer elements 10 (1), 10 (2), ..., 10 (n) of a traditional type since each consists of a rectangular plate of piezo-electric material, provided on its front and rear surfaces with electrodes (which are not shown in the figure). These elements have a width W and are arranged parallel to one another at equal distances d. The transducer elements 10 (1), ... 10 (n) have a thickness T and a length L, L/W being large. This array of elements is associated with a stage for the repeated transmission of ultrasonic signals for the excitation of the transducers. Excitation is generally achieved by the emission of trains of pulses at a predetermined frequency at a regular repetition rate. The array 10 of elements is also associated with a stage for the reception and processing of the ultrasonic echoes corresponding to obstacles encountered in their direction of propagation by the signals transmitted into the object to be examined. A branching circuit may be inserted between the array of elements and the transmission and reception stages to connect one or other of these stages selectively to the said array and thus prevent, in particular, the "blinding" of the receiving stage by the transmission stage. Protection of the receiving stage may also, and more simply, be achieved by the insertion of a diode limiter circuit at the input to this stage.

The overall configuration being thus defined, use of the Fabian-Sato diagrams relevant to the piezo-electric material concerned makes it possible to determine the geometrical characteristics of the array of transducer elements according to the invention. In fact, the (two-dimensional) diagram of curves $F \cdot T = f(W/T)$ representing the distribution of the resonant frequencies of the material concerned is examined for a vibratory mode for which, given a first predetermined working frequency F and the corresponding thickness T of the transducer elements (this thickness T having to be equal, in the case of a material which has to vibrate in the thickness mode called the $\lambda/2$ mode, to half the wavelength associated with this frequency F), there also exists, for the same material, another vibratory mode at a second frequency equal or adjacent to the frequency 2F.

The value of the ratio W/T corresponding to such a combination of two modes one of whose frequencies is double that of the other then makes it possible to determine the value of the width W of the elements, thus completing the determination of geometrical characteristics of the array of transducer elements according to the invention. To this determination it has to be added that, within the framework of the invention, the transmission stage, which incorporates a generator of excitation signals at the said first frequency F must be such that the spectrum of the transmitted signals excludes the second frequency 2F. This characteristic can be explained as follows: in order to be able to detect during reception the weak-amplitude signals at frequency 2F, it is essential to avoid transmitting signals of the same frequency which, because of their definitely greater amplitude, would mask those corresponding to the existence of the phenomenon of non-linearity. There is therefore connected at the output of the excitation-signal generator a band-pass filter centered on the first frequency F or a band-stop (band-elimination) filter centered on the second frequency 2F.

Figure 1:
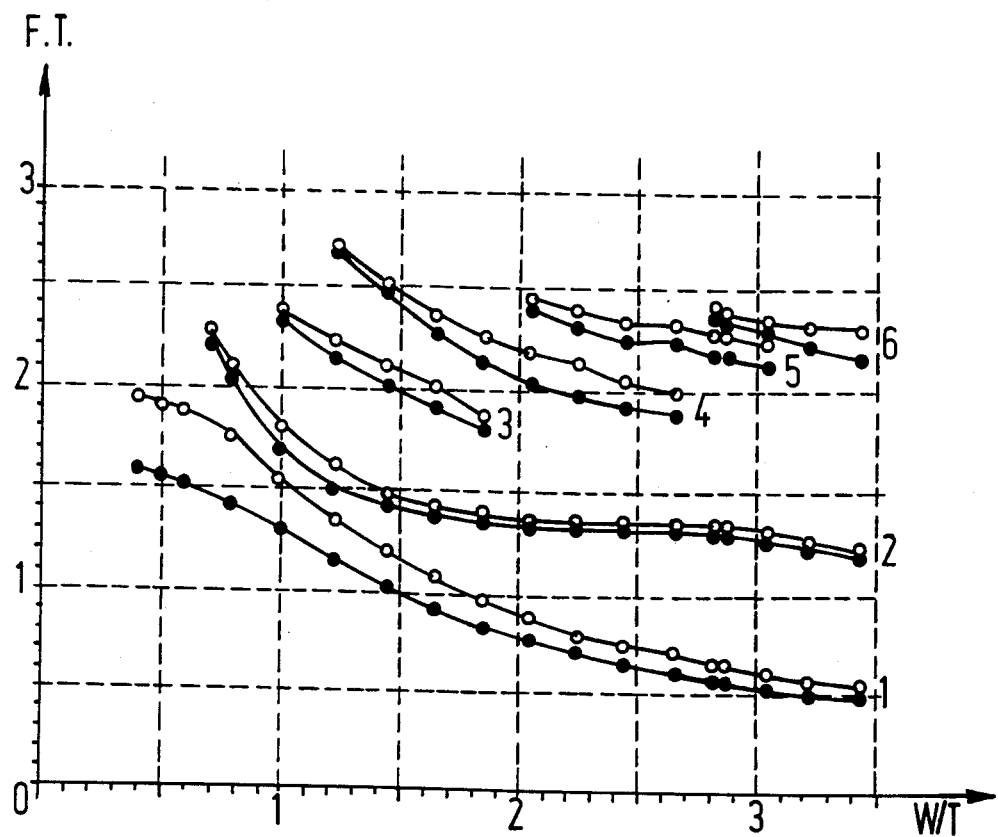

An example of the choice of transducer configuration according to the invention is given for the diagram in FIG. 1: for piezo-electric elements made of the PXE-5 material referred to above, a first frequency F of 2 megahertz, an element thickness of 0.5 millimetre and a width of 0.75 millimetre, the vibratory mode indicated as being of rank 3 in FIG. 1 in fact presents a second resonant frequency of 4 megahertz, permitting measurement during reception of the non-linearity phenomenon with which the coefficient B/A is associated.

Needless to say, the present invention is not restricted to the example of embodiment given, starting from which variants can be suggested without exceeding the framework of this invention. In particular, it should be pointed out that the invention is applicable in a strictly similar fashion to the case of three-dimensional vibratory states, when the ultrasonic transducer device is a two-dimensional array with a network of parallelepiped piezo-electric transducer elements. To that end it is sufficient to consider a three-dimensional generalization of the Fabian-Sato diagrams, the product F·T being expressed this time as a function not just of the ratio W/T but of the two geometrical-configuration ratios W/T and L/T. It is in any case obvious that a two-dimensional Fabian-Sato diagram is the limit, when L and therefore L/T become large, of such a three-dimensional Fabian-Sato diagram.

Furthermore, we have seen above that the invention was applicable particularly in the medical field for the echographic examination of tissues and more particularly the evaluation of the coefficient B/A of acoustical non-linearity of tissues thus examined and the observation of the variations of such a parameter in the interior of these tissues. In this application it may be stated that different embodiments of the circuits associated with the transducer configuration according to the invention may be suggested, and particularly those described below with reference to FIGS. 3 and 4, which show two embodiments of an apparatus for the examination of objects which can use a transducer configuration such as that described above.

The apparatus described with reference to FIG. 3 comprises, in this first embodiment, a transmitting and receiving ultrasonic transducer array 10 associated on the one hand with a transmission stage 20 intended to permit the repeated (here, periodic) transmission of ultrasonic waves by the transducer in the direction of the object to be examined and on the other hand with a receiving and processing stage 30. The transmission stage 20 caters for the transmission of the ultrasonic waves, and the spectrum of the transmission signal must not contain the frequency 2F.

The receiving and processing stage 30 comprises, first, an amplifier 50 which receives from the array 10 the electrical signals corresponding to the ultrasonic echoes received by that array, this amplifier being linked to an automatic gain control circuit 60 which increases as a function of time the gain of the said amplifier to compensate for the increasing attenuation effect on the ultrasonic waves in the course of their propagation. An interface circuit 40 may be inserted between the array 10 and the stages 20 and 30 to connect either of these stages selectively to the said array and thus prevent, in particular, "blinding" of the receiving stage by the transmission stage.

The receiving and processing stage 30 also comprises, at the output of amplifier 50, two processing channels 100 and 200 in parallel, the first of which (a conventional processing channel) comprises, in that order, a first envelope detector, consisting of a first rectifier 120 and a first low-pass filter 130, and a first display device 160, the second channel comprising, in that order, a bandpass filter 210 centered on the second frequency 2F, a second rectifier 220, a second low-pass filter 230, a comparator 240 of the outputs from low-pass filters 130 and 230, a differentiating circuit 250 and a second display device 260 (the two display devices thus provided could, of course, be replaced by a single one which would have two distinct screens, both screens being capable in all cases of being operated independently or simultaneously). This second processing channel 200 is intended to permit access to an image displaying the development of the second-order acoustic non-linearity parameter referred to as B/A.

In fact, it may be useful to recall here that during its passage through the object being studied, the transmitted train of waves generates at each point a wave of double the frequency in the same direction which is a function of the value of the coefficient B/A at this point. The biological tissues being assumed to be non-dispersive, the speed of propagation of the waves of double frequency is the same as that of the initial train of waves. Hence, the echographic signal obtained from the waves of double frequency can be compared, with the aid of the comparator 240, with the initial echographic signal. The result of this comparison, which is followed by differentiation enabling the local parameter to be estimated, thus reflects the development of parameter B/A. The images provided respectively by the first traditional channel 100 and by the second channel 200 are in the present case A-type echographs (representation of amplitudes along the ordinate as a function of time along the abscissa), but arrangements can also be made to obtain B-type echographs.

Figure 3:
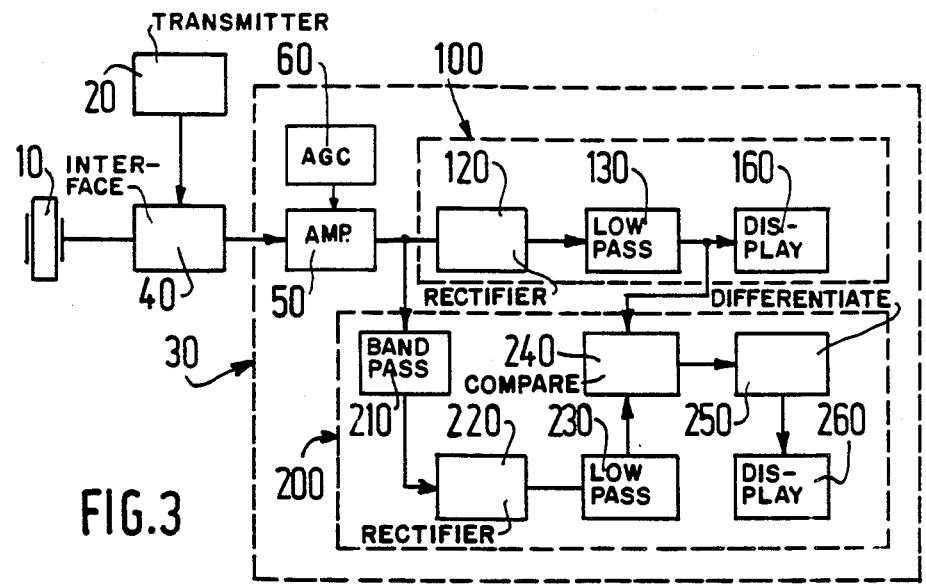
FIGS. 3 and 4 show two embodiments of an apparatus for the examination of objects capable of using a transducer configuration according to the invention.
Figure 4:
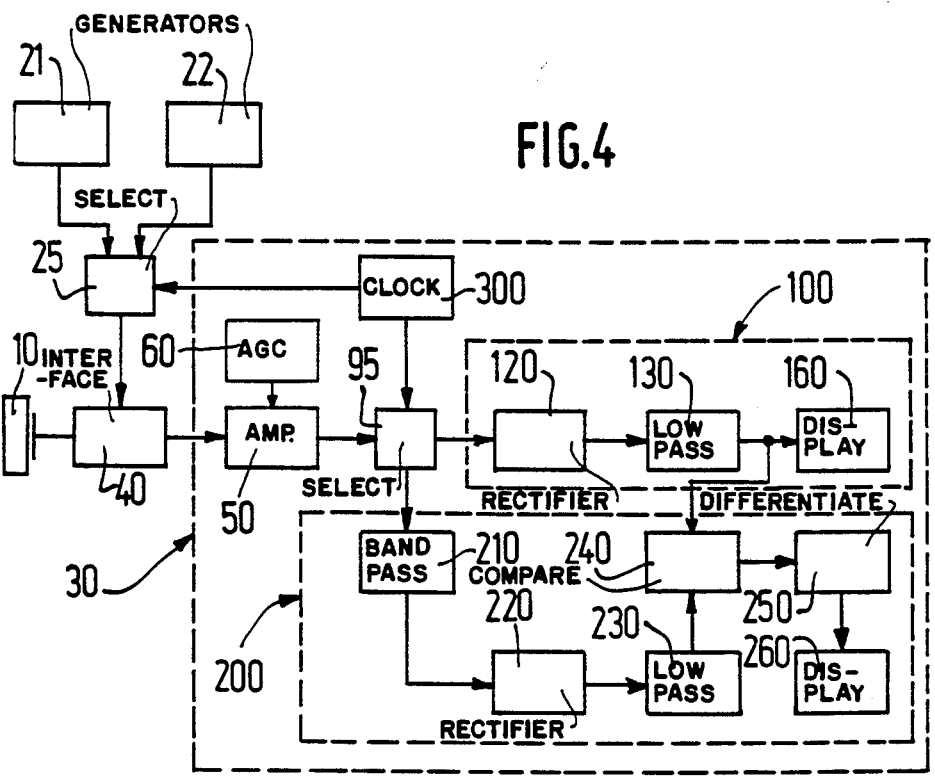

In a second embodiment shown in FIG. 4, in which the elements identical to those in the first embodiment bear the same reference numerals as in FIG. 3, the transmission stage includes a transmission-signal selection circuit 25 at the inputs of which are connected in parallel, on the one hand, a traditional generator 21 of excitation signals for the transducer array 10 (as short as possible to improve the axial resolution) and, on the other, a specialised generator 22 for measurement of B/A, i.e. supplying excitation signals which consist, on the contrary, of several sinusoids of frequency F. The receiving stage for its part, includes, between the amplification and gain-control circuit (50, 60) and the processing channels 100 and 200, a processing-selection circuit 95 to whose outputs the two processing channels are connected in parallel. These selection circuits 25 and 95 are controlled simultaneously by a clock circuit 300 to ensure synchronization of selection either of the generator 21 and the first channel 100 or the generator 22 and the second channel 200.

What is claimed is:

1. An apparatus for the examination of objects with ultrasound, comprising:
a linear array of piezo-electric transducer elements each having a width W and a thickness T, wherein the thickness T of each of the transducer elements is equal to one half of a wavelength corresponding to a first frequency F for which on a diagram of curves $F \cdot T = f(W/T)$ of the distribution of the resonant frequencies there exists a first vibratory mode at the said first frequency F and a second vibratory mode at or near a second frequency equal to 2F;
transmission means which excite the elements at the first frequency F using excitation signals having a spectrum which excludes the second frequency 2F; and
means functionally connected to the elements for receiving and processing echo signals which are received by the elements at said frequency 2F.

2. An apparatus for the examination of objects with ultrasound, comprising:
a two-dimensional array of parallelepipedic piezo-electric transducer elements each having a length L, a width W, and a thickness T, wherein the thickness T of each of the transducer elements is equal to one half of a wavelength corresponding to a first frequency F for which on a three-dimensional diagram of the curves $F \cdot T = f(W/T, L/T)$ of the distribution of the resonant frequencies there exists a first vibratory mode at the said first frequency F and a second vibratory mode at or near a second frequency equal to 2F;
transmission means which excite the elements at the first frequency F using excitation signals having a spectrum which excludes the second frequency 2F; and
means functionally connected to the elements for receiving and processing echo signals which are received by the elements at said frequency 2F.

* * * * *